US008828456B2

(12) United States Patent
Rho et al.

(10) Patent No.: US 8,828,456 B2
(45) Date of Patent: Sep. 9, 2014

(54) METHOD OF EXTERNAL SKIN APPLICATION OF COMPOSITION CONTAINING RED PINE ROOT EXTRACT

(71) Applicant: Amorepacific Corporation, Seoul (KR)

(72) Inventors: Ho Sik Rho, Yongin (KR); Eun Joo Kim, Suwon (KR); Ga Young Cho, Yongin (KR); Hye Yoon Park, Anyang (KR); Ji Seong Kim, Yongin (KR); Duck Hee Kim, Seoul (KR); Han Kon Kim, Suwon (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/756,227

(22) Filed: Jan. 31, 2013

(65) Prior Publication Data
US 2013/0129849 A1 May 23, 2013

Related U.S. Application Data

(62) Division of application No. 13/203,127, filed as application No. PCT/KR2010/001180 on Feb. 25, 2010, now abandoned.

(30) Foreign Application Priority Data

Feb. 27, 2009 (KR) ......................... 10-2009-0017074
Apr. 17, 2009 (KR) ......................... 10-2009-0033750

(51) Int. Cl.
A61K 36/00 (2006.01)
A61K 8/97 (2006.01)
A61Q 19/00 (2006.01)
A61Q 17/04 (2006.01)
A61Q 19/08 (2006.01)

(52) U.S. Cl.
CPC . A61K 8/97 (2013.01); A61Q 19/00 (2013.01); A61Q 17/04 (2013.01); A61Q 19/08 (2013.01)
USPC .......................................................... 424/725

(58) Field of Classification Search
None
See application file for complete search history.

(56) References Cited

U.S. PATENT DOCUMENTS 5,602,259 A * 2/1997 Boo et al. ....................... 549/313
5,917,084 A 6/1999 Jiang
6,060,509 A 5/2000 Jiang

FOREIGN PATENT DOCUMENTS

| CN | 1271575 | | 11/2000 |
| CN | 1271575 | A * | 11/2000 |
| CN | 1927234 | | 3/2007 |
| JP | 2003-277223 | | 10/2003 |
| KR | 10-2007-0119296 | | 12/2007 |

OTHER PUBLICATIONS

International Search Report for PCT/KR2010/001180, three pages, mailed Nov. 8, 2010.
Written Opinion for PCT/KR2010/001180, four pages, mailed Nov. 8, 2010.
Peng, Derwent accession No. 2001-169423 for CN 1271575 A (2001).
Sun, Derwent accession No. 2007-514703 for CN 1927234 A (2007).

* cited by examiner

Primary Examiner — Terry A McKelvey
Assistant Examiner — Randall Winston
(74) Attorney, Agent, or Firm — Nixon & Vanderhye PC

(57) ABSTRACT

The present invention relates to a composition for skin external application containing a pine root extract. More specifically, the composition for skin external application according to the present invention contains, as an active ingredient, a pine root extract which shows various effects, including eliminating free radicals, protecting the cell membrane from damage by UV radiation, inhibiting the production of reactive oxygen species caused by UV radiation, inhibiting the reduction in the expression of superoxide dismutase (SOD) and catalase caused by UV radiation, stimulating the production of HSP70 to protect cells, inhibiting MMP-2 biosynthesis caused by UV radiation, inducing the expression of SIRT1 gene that restores DNA damage, and inducing the expression of LMNA1 gene that maintains the structure of the nuclear membrane. Ultimately, the composition of the present invention prevents skin aging.

14 Claims, 1 Drawing Sheet

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: LMNA forward primer

<400> SEQUENCE: 1
tctgctgaga ggaacagcaa                                           20

<210> SEQ ID NO 2
<211> LENGTH: 20
<212> TYPE: DNA
<213> ORGANISM: Artificial Sequence
<220> FEATURE:
<223> OTHER INFORMATION: LMNA reverse primer -continued

```
<400> SEQUENCE: 2
ggtgatggag caggtcatct                                                    20

<210> SEQ ID NO 3
<211> LENGTH: 19
<212> TYPE: DNA
<213> ORGANISM: Artificial Sequence
<220> FEATURE:
<223> OTHER INFORMATION: SIRT1 forward primer

<400> SEQUENCE: 3
tggacaattc cagccatct                                                     19

<210> SEQ ID NO 4
<211> LENGTH: 20
<212> TYPE: DNA
<213> ORGANISM: Artificial Sequence
<220> FEATURE:
<223> OTHER INFORMATION: SIRT1 reverse primer

<400> SEQUENCE: 4
caagccgcct actaatctgc                                                    20
```

METHOD OF EXTERNAL SKIN APPLICATION OF COMPOSITION CONTAINING RED PINE ROOT EXTRACT

CROSS-REFERENCE TO RELATED APPLICATIONS

This application is a divisional of application Ser. No. 13/203,127, filed Aug. 24, 2011, pending; which is the U.S. national phase of Application No. PCT/KR2010/001180, filed Feb. 25, 2010; which designated the U.S. and claims priority to KR Application No. 10-2009-0017074, filed Feb. 27, 2009, and KR Application No. 10-2009-0033750, filed Apr. 17, 2009; the entire contents of each of which are hereby incorporated by reference.

TECHNICAL FIELD

The present invention relates to a composition for skin external application containing a pine root extract. More specifically, the composition for skin external application according to the present invention contains, as an active ingredient, a pine root extract which shows various effects, including eliminating free radicals, protecting the cell membrane from damage by UV irradiation, inhibiting the production of reactive oxygen species caused by UV radiation, inhibiting the reduction in the expression of superoxide dismutase (SOD) and catalase caused by UV radiation, stimulating the production of HSP70 to protect cells, inhibiting MMP-2 biosynthesis caused by UV radiation, inducing the expression of SIRT1 gene that restores DNA damage, and inducing the expression of LMNA1 gene that maintains the structure of the nuclear membrane. Ultimately, the composition of the present invention prevents skin aging.

BACKGROUND ART

Skin tissue contains various antioxidant systems and protective factors for protecting the skin, for example, a heat shock protein (HSP). However, it is known that skin damage occurs due to a decrease in activity caused by intrinsic aging or photoaging, and the formation of skin wrinkles and the decrease in skin elasticity occur due to an increase in the biosynthesis of matrix metalloproteinases (MMPs) that degrade skin tissue and due to a decrease in the biosynthesis of collagen, thereby inducing skin aging. Also, as a result of skin aging, DNA is damaged and the structure of the nuclear membrane is broken down, and thus restoring damaged DNA and maintaining the structure of nuclear membrane are important factors in preventing skin aging. Accordingly, it is known that antioxidant substances capable of protecting skin cells, substances capable of inhibiting the biosynthesis of MMPs that degrade the collagen of the skin, substances that prevent damage to skin cells, substances inducing the production of proteins for restoring intracellular DNA damage and proteins for maintaining the structure of the nuclear membrane, etc., relieve skin aging.

Among such substances for relieving skin aging, functional herbal materials have been constantly researched and developed in order to prevent or solve skin aging problems. Oriental skin care is based on a radical treatment method which comprises examining the human body from an overall viewpoint to understand the cause of skin aging and improve systemic conditions and fundamentally solving the cause of skin troubles to prevent the recurrence thereof.

It has been known from old times that pine trees live long without any disease to become Taoist hermits with supernatural powers. Also, pine trees have symbolized the patience and integrity of Koreans. Pine trees (*Pinus densiflora* Sieb. et Zucc.) are called another name "red pine". Various portions of red pine have different effects and have been used for diseases.

Pine trees have been called "Song-jeol" in Korean for the stem and branch knobs, "Song-keun" in Korean for young roots or root cortex, "Song-phil-du" in Korean for young branches and branch tops, "Song-yeup" in Korean for leaves, "Song-hwa-bun" in Korean for pollen, "Song-goo" in Korean for round fruits, and "Song-mok-pi" in Korean for barks, and these pine tree portions have been used for medicinal purposes.

The pine root is picked in the spring season and dried for use. In Chinese medicine, the pint tree root is known to bitter in taste, warm in nature and non-toxic. Also, it contains medicinal components, including 75% α-pinene 75%, camphene, dipentene, α-terpinenol, camphor, and p-mentanol.

In Chinese medicine, the pine root has been used to relieve the fatigue of the five viscera and treat contusion blood stasis pain, muscle/bone pain, spitting blood, and decayed tooth pain. However, the pine tree root has not been systemically studied in relation to skin aging.

Technical Problem

It is an object of the present invention to provide a composition for skin external application which contains, as an active ingredient, a pine root extract which shows an excellent effect of preventing skin aging.

Technical Solution

A composition for skin external application according to the present invention contains a pine root extract.

Also, the composition for skin external application according to the present invention is used to prevent skin aging.

Also, the composition for skin external application according to the present invention is used to protect the cell membrane from damage caused by UV radiation.

Also, the composition for skin external application according to the present invention is used to protect cells that promote the production of HSP70 protein.

Also, the composition for skin external application according to the present invention is used to inhibit the biosynthesis of MMP-2 caused by UV radiation.

Also, the composition for skin external application according to the present invention is used to induce the expression of SIRT1 gene that restores DNA damage and the expression of LMNA1 gene that maintains the structure of the nuclear membrane.

Also, the composition for skin external application according to the present invention is used to alleviate skin wrinkles.

Also, the composition for skin external application according to the present invention is used to promote skin regeneration.

Advantageous Effects

The composition for skin external application according to the present invention contains a pine root extract. Thus, the composition of the present invention has the effect of inhibiting photoaging caused by UV radiation and shows the effect of secreting regulatory substances resisting excessive intrinsic or extrinsic stresses in cells to prevent cell damage from occurring. Also, the composition of the present invention is excellent in the effect of inhibiting MMP activity, which is an index of skin anti aging. Moreover, the composition of the present invention has excellent effects of inducing the expression of SIRT1 gene that restores DNA damage and inducing the expression of LMNA1 gene that maintains the structure of the nuclear membrane. Accordingly, the inventive composition for skin external application containing a pine root extract alleviates skin wrinkles to inhibit skin aging.

BEST MODE

Figure 1:
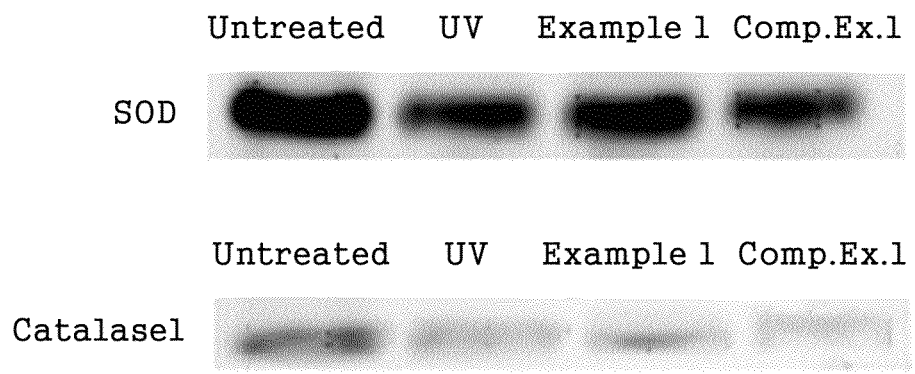
FIG. 1 shows the effect of the inventive pine root (red pine root) extract on the expression of SOD and catalase.

Red pine which is used in the present invention is *pinus densiflora* Siebold et Zuccarini) belonging to the family Pinaceae, and is bitter in taste and warm in nature and no-toxic. It acts on the spleen meridian and the heart meridian and has been used long ago to treat a swelling caused by wind/dampness, Tinea cruris, leprosy, incised wound, etc.

The pine root extract which is used in the present invention can be prepared by extracting the root of red pine in a solvent such as an aqueous ethanol solution according to a conventional method known in the art. Alternatively, the sap of the pine root may be directly used without any treatment.

The composition for skin external application according to the present invention may contain the pine root extract in an amount of 0.001-99 wt % based on the total weight of the composition.

The composition for skin external application according to the present invention contains a cosmetically and skin-scientifically acceptable medium and/or base. The composition may be formulated as a preparation for local application. Examples of formulations for local application include solution, gel, solid or dough anhydride, emulsion prepared by dispersing oil phase in water phase, suspension, microemulsion, microcapsule, microgranule, ionic (liposome) and/or non-ionic vesicle, cream, skin, lotion powder, spray, and conceal stick. In addition, the composition of the present invention can be formulated according to a conventional method known in the art. Also, the composition for skin external application according to the present invention can be formulated as a foam composition or an aerosol composition further containing a compressed propellant.

The composition for skin external application according to the present invention may contain additives which are conventionally field in the cosmetic field or the skin science field, for example, fatty substance, organic solvent, resolvent, thickener, gelling agent, softener, antioxidant, suspending agent, stabilizer, foaming agent, aromatic, surfactant, water, ionic or non-ionic emulsifying agent, filler, sequestering agent, chelating agent, preserving agent, vitamins, blocker, moisturizing agent, essential oil, dye, pigment, hydrophilic or hydrophobic activator, lipid vesicle or other components. These additives are contained in amounts which are generally used in the cosmetic field or the skin science field.

Mode For Invention

Hereinafter, the present invention will be described in further detail with reference to examples and test examples. It is to be understood, however, that these examples are for illustrative purposes only and are not to be construed to limit the scope of the present invention. Also, those skilled in the art will appreciate that various modifications, additions and substitutions are possible, without departing from the scope and spirit of the present invention as disclosed in the accompanying claims.

EXAMPLE 1

Preparation of Pine Root (Red Pine Root) Extract 1 kg of pine roots were added to 5 liters of 80% ethanol aqueous solution, and extracted three times under reflux, and then dipped at 15° C. for 1 day. Then, the extract was filtered through filter cloth and centrifuged to separate it into residue and the filtrate. The separated filtrate was concentrated under reduced pressure, thus obtaining 173 g of a pine root extract.

COMPARATIVE EXAMPLE 1

Preparation of Red Pine Leaf Extract 1 kg of red pine leaves were added to 0.5 liters of 80% ethanol aqueous solution, and extracted three times under reflux, and then dipped at 15° C. for 1 day. Then, the extract was filtered through filter cloth and centrifuged to separate it into residue and the filtrate. The separated filtrate was concentrated under reduced pressure, thus obtaining 0.1 g of a red pine root extract.

TEST EXAMPLE 1

Free Radical Removal Activity

To measure antioxidant activity, the 1,1-diphenyl-2-pycryl-hydrazyl (DPPH) method was used. Specifically, each of the extracts obtained in Example 1 and Comparative Example 1 was diluted in ethanol to varying concentrations (0, 50, 100, 200, 300 and 400 µg/mL), and 10 µl of each dilution was added to each well of a 96-well plate. A solution of 5 mM DPPH in ethanol was added to each well to a total volume of 200 µl. The resulting solution was incubated at 37° C. for 30 minutes, and then measured at 520 nm using an ELISA reader (DI Biotech, Korea). Based on the measured absorbance, free radical removal activity was calculated according to the following Equation 1. As a positive control, vitamin C known to have excellent antioxidant activity was used. The test results are shown in Table 1 below.

Radical removal activity (%)=absorbance of control-absorbance of sample/absorbance of control×100    Equation 1

TABLE 1

| Treatment | Radical Removal Activity (%) | | |
| --- | --- | --- | --- |
| Concentration | Ex. 1 | Comp. Ex. 1 | Vitamin C |
| 0 µg/mL | 0 | 0 | 0 |
| 50 µg/mL | 24 | 10 | 30 |
| 100 µg/mL | 61 | 35 | 90 |
| 200 µg/mL | 75 | 60 | 91 |
| 300 µg/mL | 83 | 79 | 90 |
| 400 µg/mL | 87 | 80 | 90 |

As can be seen in Table 1 above, the pine root (red pine root) extract of Example 1 showed excellent radical removal activity compared to the red pine leaf extract of Comparative Example 1. As the concentration of the extract of Example 1 was increased, the extract of Example 1 showed radical removal activity comparable to that of vitamin C known as a powerful antioxidant.

TEST EXAMPLE 2

Measurement of Cell Membrane Against Damage

100 μl of a human keratinocyte HaCaT cell line obtained from the German Cancer Research Center (Heidelberg, Germany) was added to each well of a 96-well plate at a density of $1 \times 10^5$ cells/mL and cultured in a 5% CO2 incubator at 37° C. Then, cultures each containing each of the extracts of Example 1 and Comparative Example 1 at varying concentrations of 0.625, 1.25, 2.5 and 5 μg/mL were added to each well and cultured for 3 hours. After 3 hours, 50 μl of the culture broth was removed, and phosphate buffered saline was added to each well. Each well was irradiated with 30 mJ/cm$^2$ of UV light using a UV-B lamp, followed by removal of the phosphate buffered saline. Then, 200 μl of each of the cell cultures containing the extract at the above concentrations was added to each well and cultured for 24 hours. After 24 hours of the culture, a suitable amount of the supernatant of each culture was taken, and the amount of lactate dehydrogenase (LDH), an index of cell damage, was measured using a cytotox 96 non-radioactive cytotoxicity assay kit. The measurement was repeated six times and averaged. The measurement results are shown in Table 2 below. Herein, a control group was a group treated with neither the extract of Example 1 nor the extract of Comparative Example 1.

TABLE 2

| Test Materials | | Control Group Comparison Ratio (%) |
|---|---|---|
| Control Group | | 100 |
| Control Group + UV Irradiation | | 222.4 |
| Example 1 + UV Irradiation | 0.625 μg/mL | 206.1 |
| | 1.25 μg/mL | 151.2 |
| | 2.5 μg/mL | 132.8 |
| | 5 μg/mL | 102.5 |
| Comp. Ex. 1 + UV Irradiation | 0.625 μg/mL | 214.3 |
| | 1.25 μg/mL | 205.6 |
| | 2.5 μg/mL | 179.2 |
| | 5 μg/mL | 153.2 |

As can be seen from the results in Table 2 above, in the group treated with the pine root extract of Example 1 at varying concentrations and irradiated with UV B light, the increase in the activity of LDH in the cell culture, caused by UV-B irradiation, was inhibited in a concentration-dependent manner, and the effect of the extract of Example 1 in the group was significantly excellent compared to that in the group treated with the same amount of the red pine leaf extract (Comparative Example 1). Particularly, it could be seen that level of LDH in the group treated with 5 μg/mL of the pine root extract can was inhibited to the level of LDH in the control group not irradiated with UV-B light. Such results suggest that the pine root extract of Example 1 according to the present invention can effectively inhibit damage to the membrane of the HaCaT cells, caused by UV-B irradiation.

TEST EXAMPLE 3

Inhibition of Production of Reactive Oxygen Species

100 μl of human keratinocyte HaCaT cells were added to each well of a 96-well black plate for fluorescent measurement at a density of $2.0 \times 10^5$ cells/mL and cultured in a 5% CO$_2$ incubator at 37° C. for 24 hours. Then, the cells were treated with each of the extracts of Example 1 and Comparative Example 1. The extracts were used at varying concentrations of 0.625, 1.25, 2.5 and 5 μg/mL. After the cells have been cultured together with each extract for 24 hours, each well was washed with HCSS (HEPES-buffered control salt solution) to remove the remaining medium, and 100 μl of a solution of 20 μM DCFH-DA (2',7'-dichlorodihydro-fluorescein diacetate) in HCSS was added to each well. Then, the cells were cultured in a 5% CO$_2$ incubator at 37° C. for 20 minutes and washed again with HCSS. Then, 100 μl of HCSS solutions, each containing each extract at varying concentrations, was added to each well, and each well was irradiated with UV B light (30 mJ/cm$^2$). After 3 hours, the fluorescence strength of each well was measured with a fluorometer (Ex=485 nm; Em=530 nm), and the measurement results are shown in Table 3. The measurement was repeated six times and averaged. Herein, a control group was a group treated with neither the extract of Example 1 nor the extract of Comparative Example 1.

TABLE 3

| Test Materials | | Control Group Comparison Ratio (%) |
|---|---|---|
| Control Group | | 100 |
| Control Group + UV Irradiation | | 182.1 |
| Example 1 + UV Irradiation | 0.625 μg/mL | 140.3 |
| | 1.25 μg/mL | 137.2 |
| | 2.5 μg/mL | 132.1 |
| | 5 μg/mL | 104.2 |
| Comp. Ex. 1 + UV Irradiation | 0.625 μg/mL | 168.6 |
| | 1.25 μg/mL | 155.3 |
| | 2.5 μg/mL | 144.2 |
| | 5 μg/mL | 132.6 |

As can be seen from the results in Table 3 above, at 3 hours after UV irradiation, the level of intracellular reactive oxygen species in the group irradiated with UV B light were increased by 182.1% compared to the control group not irradiated with UV light. This increase was inhibited in a concentration-dependent manner when the cells were treated with the pine root extract of Example 1 at varying concentrations. Such results suggest that the pine root extract of Example according to the present invention inhibits the production of intracellular reactive oxygen species caused by UV irradiation. Also, the inhibitory effect of the extract of Example 1 on the production of reaction oxygen species was excellent compared to that of the red pine leaf extract of Comparative Example 1.

TEST EXAMPLE 4

Recovery from Reduction in Expression of SOD (Superoxide Dismutase) and Catalase 2 ml of human keratinocyte HaCaT cells were added to each well of a 6-well plate at a density of $1 \times 10^5$ cells/mL and cultured in a CO$_2$ incubator at 37° C. for 24 hours. Then, the cells were treated with each of the extracts of Example 1 and Comparative Example 1 at a concentration of 5 μg/mL and cultured for 24 hours. Then, each well was washed with phosphate buffered saline to remove the remaining culture medium and irradiated with UV B light. Then, the phosphate buffered saline was removed, and the cells were treated with each extract and cultured for 48 hours. After 48 hours of the culture, the cells were collected and lysed with lysis buffer (containing 250 mM NaCl, 25 mM Tris-HCl pH 7.5, 5 mM EDTA pH 8.0, 1% NP-40, 0.1 M PMSF, 1 M DTT, protease inhibitor cocktail, and deionized water (DW)) at 4° C. Then, proteins were quantified using BCA reagent. Equivalent amounts of proteins were mixed with a buffer containing each extract to prepare samples, which were then separated by electrophoresis on sodium dodesyl sulfate (SDS) polyacrylamide gel. For Western blot analysis, the acrylamide gel containing the separated proteins was transferred to a nitrocellulose membrane by electroblotting, and then washed twice with TBS-T (0.1% Tween 20 in TBS) containing 5% skim milk. After washing, the membrane was treated with each of anti-SOD and anti-catalase primary antibodies (1:2,000), incubated at 4° C. for 12 hours, and then incubated with secondary antibodies corresponding to the primary antibodies (1:2,000) at room temperature for 1 hour. The membrane was washed with TBS-T, and then an ECL (enhanced chemiluminescence) solution was applied thereto. Then, the membrane was sensitized to an X-ray film in a dark room, and the expression patterns of SOD and catalase were comparatively analyzed. In order to confirm whether equal amounts of the proteins were loaded, the above analysis procedure was repeated using actin as primary antibody. The analysis results are shown in FIG. 1.

The expressions of SOD and catalase were observed 48 hours after irradiating the HaCaT cells with UV B light. As a result, as shown in FIG. 1, the expressions of SOD and catalase were significantly reduced, and when the cells were treated with 5 μg/mL of the extract of the pine root (red pine extract) of Example 1, the reduction in the expression of the antioxidant enzymes caused by UV light was effectively inhibited. This inhibitory effect of the pine root extract of Example 1 was excellent compared to that of Comparative Example 1. Such results suggest that the pine root extract according to the present invention shows an antioxidant effect by itself, and also has an excellent effect of protecting intracellular antioxidant enzyme systems against damage caused by endogenous or exogenous oxidative stress, indicating that the pine root extract has a function of protecting cells.

TEST EXAMPLE 5

Cell Protection Effect

Figure 2:
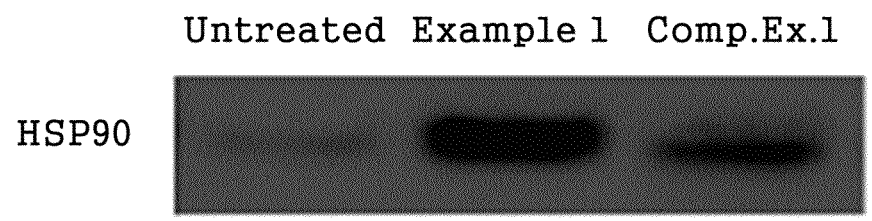
FIG. 2 shows the effect of the inventive pine root (red pine root) extract on the expression of HSP70 protein.

It is known that the protein HSP70 which is induced in response to stress protects cells individuals against various stresses and also prevents apoptosis. Also, it is known that the over-expressed HSP70 protein protects cells from stress or various toxicities. To measure cell protection resulting from the promotion of HSP70 production, 2 ml of normal fibroblasts were added to each well of a 6-well plate at a density of $1 \times 10^5$ cells/mL and cultured in a 5% $CO_2$ incubator at 37° C. for 24 hours. Then, the cells were treated with 1 μg/mL of each of the extracts of Example 1 and Comparative Example 1, cultured for 24 hours and lysed with lysis buffer at 4° C. Then, proteins were quantified with BCA reagent. Equivalent amounts of proteins were mixed with a buffer containing each extract to prepare samples, which were then separated by electrophoresis on sodium dodesyl sulfate polyacrylamide gel. For Western blot analysis, the acrylamide gel containing the separated proteins was transferred to a nitrocellulose membrane by electroblotting, and then stained with Ponceau S to conform that equal amounts of proteins have been transferred. The membrane to which the proteins were transferred was incubated in TBS-T (0.1% Tween 20 in TBS) containing 5% skim milk at room temperature for 1 hour to block non-specific proteins and was washed twice with TBS-T. After washing, the membrane was treated with HSP70 primary antibody (1:1,000), incubated overnight at 4° C., and then incubated with secondary antibody (1:2,000) corresponding to the primary antibody at room temperature for 1 hour. The membrane was washed with TBS-T, and then an ECL (enhanced chemiluminescence) solution was applied thereto. Then, the membrane was sensitized to an X-ray film in a dark room, and the expression patterns of HSP70 protein were comparatively analyzed. The analysis results are shown in FIG. 2.

As can be seen from the results in Table 2 above, in the group treated with 1 μg/mL of the pine root extract of Example 1, the production of HSP70 protein was significantly induced, and the production of HSP70 protein was induced in a concentration-dependent manner. Accordingly, it can be considered that the pine root (red pine root) extract according to the present invention expresses the HSP70 protein at a given level or higher and can show the effect of protecting cells against stresses. Also, the effect of the pine root extract of the present invention on cell protection was excellent compared to the red pine leaf extract of Comparative Example 1.

TEST EXAMPLE 6

Inhibition of MMP-2 Biosynthesis

It is assumed that, if cultured skin cells and human skin is irradiated with UV light, the expression of various matrix metalloproteinases will be increased and the increased MMPs degrade the collagen of the skin to form skin wrinkles. According to this assumption, in order to test the effect of the pine root extract on the inhibition of ECM damage caused by UV light using a method of evaluating the degree of aging of aged cells and increasing the amount of the deficient collagen of aged akin, 2 ml of normal fibroblasts were added to each well of a 6-well plate at a density of $1 \times 10^5$ cell/mL and cultured in a 5% $CO_2$ incubator at 37° C. for 24 hours. Then, each of the extracts of Examples 1 and Comparative Example 1 was added to the cells at varying concentrations of 0.25, 0.5 and 1 μg/mL. Then, the cells were irradiated with 30 mJ/cm$^2$ of UV B in the same manner as described in Example 5, and then treated with the pine root extract and cultured for 24 hours. Then, the cell culture was collected and mixed with a buffer containing the pine root extract to prepare samples, which were then loaded onto zymogram gel containing gelatin. Then, proteins on the zymogram gel were separated by electrophoresis. To identify MMP-2, the zymogram gel containing the separated proteins was incubated at room temperature for 30 minutes in renaturing buffer (2.7% Triton X-100) according to the manufacturer's instruction and incubated in developing buffer [containing 50 mM Tris Base, 40 mM 6N HCl, 200 mM NaCl, 5 mM $CaCl_2 \cdot 2H_2O$, BriJ 35 0.02%] at room temperature overnight. Then, the gel was incubated in fresh developing buffer at 37° C. overnight. The incubated gel was stained to determine the degree of biosynthesis of MMP-2. In order to confirm that there was no difference between the samples, the cells were collected, lysed with lysis buffer at 4° C., transferred to a nitrocellulose membrane by electroblotting, and then stained with Ponceau S to confirm that equal amounts of proteins were transferred. The test results are shown in Table 4 below.

TABLE 4

| Test Materials | | Control Group Comparison Ratio (%) |
|---|---|---|
| Control Group | | 100 |
| Example 1 | 0.25 µg/mL | 77.2 |
| | 0.5 µg/mL | 76.1 |
| | 1 µg/mL | 49.6 |
| Comp. Ex. 1 | 0.25 µg/mL | 89.3 |
| | 0.5 µg/mL | 80.5 |
| | 1 µg/mL | 62.5 |

As can be seen from the results in Table 4 above, when the cells were treated with 1 µg/mL of the pine root extract of Example 1, the biosynthesis of MMP-2 was inhibited in a concentration-dependent manner. Also, this inhibitory effect of the pine root extract of Example was excellent compared to that of the red pine leaf extract of Comparative Example 1. This suggests that the pine root extract of Example 1 can inhibit the biosynthesis of MMP-2 caused by UV light and inhibit ECM damage caused by UV light so as to inhibit wrinkle formation, thereby inhibiting skin aging.

TEST EXAMPLE 7

Effect of Inducing Expression of SIRT1 and LMNA1 Genes

Human keratinocyte HaCaT cells received from the Korean Cell Line Bank (Seoul, Korea) were added to DMEM medium (containing 10% (v/v) FBS, penicillin 100 U/ml and streptomycin 100 µg/ml) and cultured in a 5% $CO_2$ animal cell incubator at 37° C. The HaCaT cells prepared at a concentration of $1.5 \times 10^6$ cells/well were adapted to FBS-free medium for 3 hours, treated with 10 ppm of each of the extracts of Example 1 and Comparative Example 1, and incubated for 24 hours. Total RNA was extracted using TRIzol™ (GIBCO BRL, Maryland, USA) and stored at −80° C. 1 g of total RNA was added to 25 liters of reverse transcriptase reaction buffer (containing 50 mM Tris-HCl, pH 8.3, 75 mM KCl, 3 mM $MgCl_2$, 0.1 M DTT, 10 mM dNTP and 40 U/l RNase inhibitor). 0.5 g/l oligo $(dT)_{16}$ primer and 200 U SuperScript II (GiboBRL) reverse transcriptase were added thereto and allowed to react at 42° C. for 1 hour. Then, 2.5 µl of the reverse transcriptase reaction solution was added to 50 µl of PCR reaction buffer (containing AmpliTaq DNA polymerase [0.04 U, Perkin Elmer, Connecticut, USA], 50 mM Tris (pH 8.3), 0.25 mg/ml bovine fetal albumin, 3 mM $MgCL_2$ and 0.25 mM dNTPs) and amplified using 10 M primers in the following conditions: 30 cycles of denaturation at 94° C. for 30 sec, annealing at 53° C. for 30 sec and extension at 72° C. for 1 min. The amplification product was electrophoresed on 1% agarose gel and imaged. Each of the primers was constructed based on SCI papers, and the sequences of the primers are shown in Table 5 below.

TABLE 5

| SEQ ID NO | Names | Sequences |
|---|---|---|
| 1 | LMNA Forward | 5'-TCT GCT GAG AGG AAC AGC AA-3' |
| 2 | LMNA Reverse | 5'-GGT GAT GGA GCA GGT CAT CT-3' |
| 3 | SIRT1 Forward | 5'-TGG ACA ATT CCA GCC ATC T-3' |
| 4 | SIRT1 Reverse | 5'-CAA GCC GCC TAC TAA TCT GC-3' |

Figure 3:
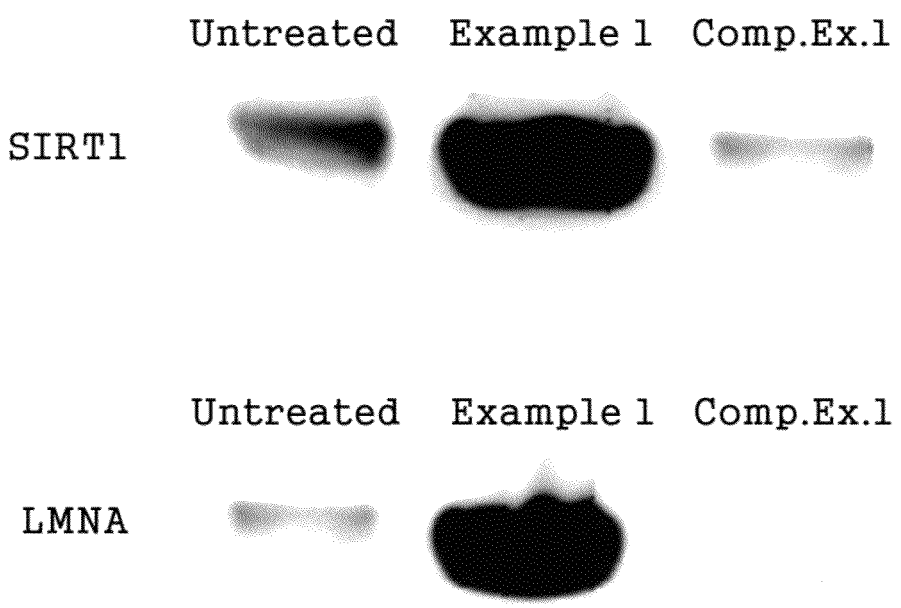
FIG. 3 shows the effect of the inventive pine root (red pine root) extract on the expression of SIRT1 gene and LMNA1 gene.

The test results are shown in FIG. 3. As can be seen in FIG. 3, when the cells were treated with 1 µg/mL of the pine root extract of Example 1, the expression of the SIRT1 gene that restores DNA damage caused by aging and the expression of the LMNA1 gene that maintains the nuclear membrane structure providing a barrier for DNA were induced, and the gene expression-inducing effect of the pine root extract of Example 1 was excellent compared to that of the red pine leaf extract. This suggests that the pine root extract of the present invention can induce the expression of the SIRT1 and LMNA1 genes, thus restoring DNA damage caused by aging and maintaining the nuclear membrane structure providing a barrier for DNA.

FORMULATION EXAMPLES 1 TO 3 AND COMPARATIVE FORMULATION EXAMPLES 1 AND 2

According to the compositions shown in Table 6 below, cream of Formulation Examples 1 to 3 and Comparative Formulation Examples 1 and 2 were prepared by completely dissolving an oily phase and an aqueous phase at 70° C. and emulsifying the solution at 7,000 rpm for 5 minutes (unit: wt %).

TABLE 6

| | Ingredients | Formul. Ex. 1 | Formul. Ex. 2 | Formul. Ex. 3 | Comp. Formul. Ex. 1 | Comp. Formul. Ex. 2 |
|---|---|---|---|---|---|---|
| Oil Phase | Bees wax | 2 | 2 | 2 | 2 | 2 |
| | Stearyl alcohol | 5 | 5 | 5 | 5 | 5 |
| | Stearic acid | 8 | 8 | 8 | 8 | 8 |
| | Squalene | 10 | 10 | 10 | 10 | 10 |
| | Propylene glycol Monostearate | 3 | 3 | 3 | 3 | 3 |
| | Polyoxyethylene ether | 1 | 1 | 1 | 1 | 1 |
| | Antiseptics, Antioxidants | q.s. | q.s. | q.s. | q.s. | q.s. |

TABLE 6-continued

| | Ingredients | Formul. Ex. 1 | Formul. Ex. 2 | Formul. Ex. 3 | Comp. Formul. Ex. 1 | Comp. Formul. Ex. 2 |
|---|---|---|---|---|---|---|
| Water Phase | Glycerin | 4 | 4 | 4 | 4 | 4 |
| | Propylene glycol | 8 | 8 | 8 | 8 | 8 |
| | Triethylamine | 1 | 1 | 1 | 1 | 1 |
| | Sodium polyacrilate | 0.2 | 0.2 | 0.2 | 0.2 | 0.2 |
| | Purified water | To 100 | To 100 | To 100 | To 100 | To 100 |
| | Pine Root extract of Ex. 1 | 0.001 | 1 | 10 | — | — |
| | Red Pine leaf Extract of Comp. Ex. 1 | — | — | — | 10 | — |

TEST EXAMPLE 8

Effect of Reducing Skin Wrinkles

The skin wrinkle-reducing effects of Formulation Examples 2 and 3 and Comparative Examples 1 and 2 were evaluated on human subjects.

On 25 women subjects (30-50 years old), the cream prepared in Formulation Example 2 was applied to the right side of the face, and the cream prepared in Comparative Formulation Example 2 was applied to the left side of the face. The application of the cream was performed twice a day for 6 weeks. On other women subjects (30-50 years old), the cream prepared in Formulation Example 3 was applied to the right side of the face, and the cream prepared in Comparative Formulation Example 1 was applied to the left side of the face. The application of the cream was performed twice a day for 6 weeks. After 6 weeks, wrinkles around the outer corner of the eye were taken with a replica, and the conditions thereof and compared with the conditions of skin wrinkles taken before the use of the cream, using a skin visiometer and a skin image analyzer. The results are shown in Table 7 below.

TABLE 7

| Evaluation Items | Formul. Ex. 2 | | Comp. Formul. Ex. 2 | | Formul. Ex. 3 | | Comp. Formul. Ex. 1 | |
|---|---|---|---|---|---|---|---|---|
| | Before Use | 6 Weeks Later | Before Use | 6 Weeks Later | Before Use | 6 Weeks Later | Before Use | 6 Weeks Later |
| Average Wrinkle Depth (μm) | 20.8 | 18.4 | 20.7 | 20.2 | 20.7 | 17.5 | 20.6 | 19.3 |
| Wrinkle Reduction of After Use to Before Use | 11.53% | | 2.41% | | 15.45% | | 6.31% | |

As can be seen from the results in Table 7 above, when the cream of Formulation Examples 2 and 3 containing the pine root extract of the present invention were applied to the face of the women subjects, the effects of reducing skin wrinkles around the outer corner of the eye were excellent compared to those of Comparative Formulation Examples 1 and 2.

We claim:

1. A method of treating aged wrinkled skin in a subject, the method comprising applying a composition externally to the aged wrinkled skin of said subject; wherein the composition contains pine root extract in an amount effective to reduce wrinkles and the pine root extract is prepared by extracting *Pinus densiflora* Siebold et Zuccarini root in solvent to obtain active ingredients in solution, filtering and separating the solution to obtain a filtrate, and concentrating the filtrate.

2. A method of treating aged wrinkled skin in a subject, the method comprising applying a composition externally to the aged wrinkled skin of said subject; wherein the composition contains pine root extract in an amount effective to reduce wrinkles and the pine root extract is prepared by extracting *Pinus densiflora* Siebold et Zuccarini root in aqueous ethanol to obtain active ingredients in solution, filtering and separating the solution to obtain a filtrate, and concentrating the filtrate.

3. The method according to claim 1, wherein cell membranes are protected from damage caused by UV radiation.

4. The method according to claim 1, wherein cells that promote production of HSP70 protein are protected.

5. The method according to claim 1, wherein biosynthesis of MMP-2 caused by UV radiation is inhibited.

6. The method according to claim 1, wherein gene expression of SIRT1 to restore DNA damage and gene expression of LMNA1 to maintain the structure of the nuclear membrane are induced.

7. The method according to claim 1, wherein skin wrinkles are alleviated.

8. The method according to claim 1, wherein skin regeneration is promoted.

9. The method according to claim 2, wherein cell membranes are protected from damage caused by UV radiation.

10. The method according to claim 2, wherein cells that promote production of HSP70 protein are protected.

11. The method according to claim 2, wherein biosynthesis of MMP-2 caused by UV radiation is inhibited.

12. The method according to claim 2, wherein gene expression of SIRT1 to restore DNA damage and gene expression of LMNA1 to maintain the structure of the nuclear membrane are induced.

13. The method according to claim 2, wherein skin wrinkles are alleviated.

14. The method according to claim 2, wherein skin regeneration is promoted.

* * * * *